(12) United States Patent
Bourke et al.

(10) Patent No.: US 8,021,367 B2
(45) Date of Patent: Sep. 20, 2011

(54) TOE DEFORMITY REPAIR USING BIOABSORBABLE PIN

(75) Inventors: Gerard Bourke, Melbourne (AU);
Mihaela Morar, Fort Myers, FL (US);
Peter A. Denove, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1020 days.

(21) Appl. No.: 11/867,586

(22) Filed: Oct. 4, 2007

(65) Prior Publication Data
US 2008/0086139 A1    Apr. 10, 2008

Related U.S. Application Data

(60) Provisional application No. 60/849,022, filed on Oct. 4, 2006.

(51) Int. Cl.
*A61B 17/86* (2006.01)
(52) U.S. Cl. ...................................... 606/86 A
(58) Field of Classification Search .............. 606/59, 606/60, 304, 309, 329, 331, 86 R, 311, 908; 623/21.19
See application file for complete search history.

(56) References Cited

U.S. PATENT DOCUMENTS

| | | | | |
|---|---|---|---|---|
| 4,944,742 A * | 7/1990 | Clemow et al. | ................ | 606/59 |
| 4,969,909 A * | 11/1990 | Barouk | ................ | 623/21.15 |
| 5,201,733 A * | 4/1993 | Etheredge, III | ................ | 606/53 |
| 5,207,712 A * | 5/1993 | Cohen | ................ | 623/21.19 |
| 5,326,366 A * | 7/1994 | Pascarella et al. | ................ | 623/21.19 |
| 5,843,085 A * | 12/1998 | Graser | ................ | 606/87 |
| 7,041,106 B1 * | 5/2006 | Carver et al. | ................ | 606/309 |

* cited by examiner

*Primary Examiner* — Thomas C Barrett
*Assistant Examiner* — Christian Sevilla
(74) *Attorney, Agent, or Firm* — Dickstein Shapiro LLP

(57) ABSTRACT

Methods and apparatus for repair of toe deformities using a bioabsorbable pin. The apparatus is a kit of part comprising a bioabsorbable pin, a predrill, a bone tamp, a cutter and a forceps. One surgical method of repairing toe deformities includes resecting a proximal interphalangeal joint, drilling a hole in a proximal phalanx using a proximal portion of a pin, removing the pin from the proximal phalanx, drilling a tip of a toe through middle and distal phalanxes, driving the pin retrograde and traversing the distal, middle and proximal phalanxes until the pin stops advancing due to resistance at a proximal cortex, holding the pin and powering a pin driver to separate a distal portion of the pin, and suturing the wound.

9 Claims, 11 Drawing Sheets

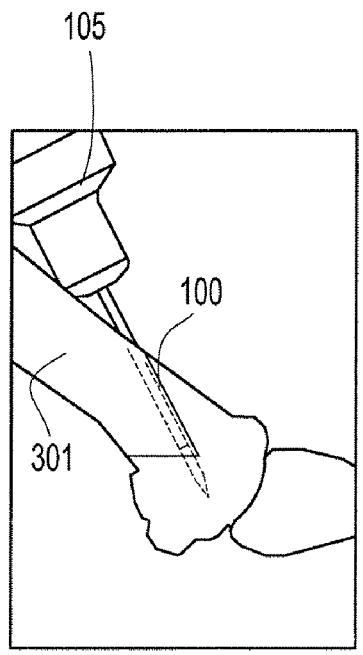
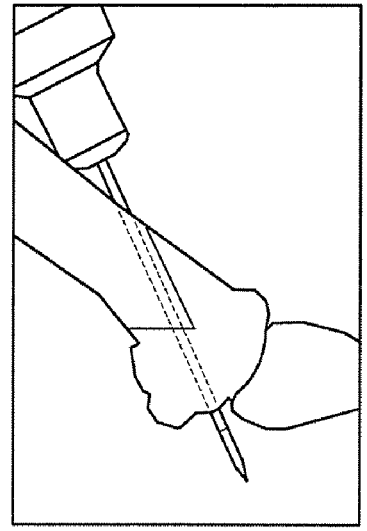
FIG. 2C  FIG. 2D
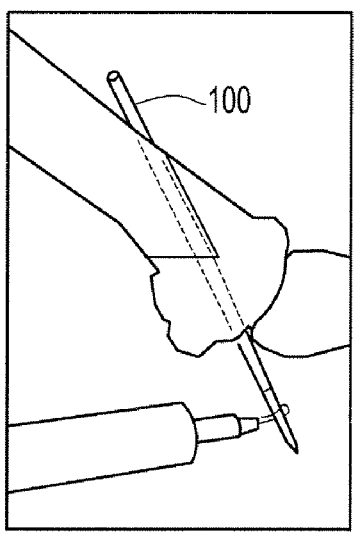
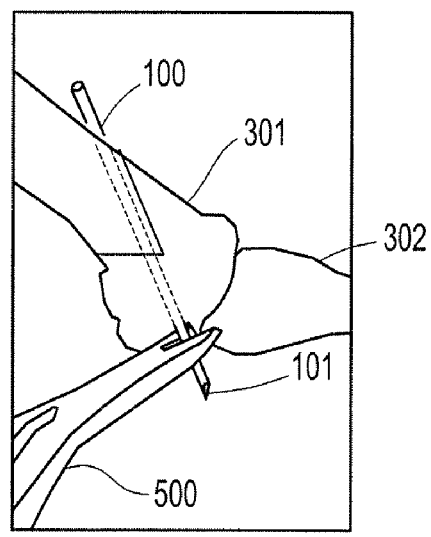
FIG. 2E  FIG. 2F

TOE DEFORMITY REPAIR USING BIOABSORBABLE PIN

CROSS-REFERENCE TO RELATED APPLICATIONS

This application claims priority to U.S. Provisional Application No. 60/849,022, filed on Oct. 4, 2006, the entire disclosure of which is hereby incorporated by reference.

BACKGROUND OF THE INVENTION

1. Field of the Invention

The present invention relates to the field of surgery and, in particular, to an apparatus and surgical methods for repairing deformities in the proximal, middle or distal phalanx of the toe.

2. Description of the Related Art

A human forefoot consists of five metatarsals and five toes. Each toe of a foot consists of three bones, except for the big toe which consists of two. The three bones of each toe are the proximal phalanx, the middle phalanx and the distal phalanx, except the big toe which has only distal and proximal phalanxes/phalanges.

The joints of the forefoot are: (i) metatarsal phalangeal (MTP) joint; (ii) proximal interphalangeal (PIP) joint; and (iii) distal interphalangeal (DIP) joint. The MTP joint is the joint between the metatarsal and the proximal phalanx of the adjacent toe. The PIP joint is the joint between the proximal phalanx and the middle phalanx of each toe. The DIP joint is the joint between the middle phalanx and the distal phalanx of each toe.

The common deformities associated with the forefoot are hammer toes, claw toes and mallet toes. A hammertoe is a deformity of the second, third or fourth toes. In this condition, the toe is bent at the middle joint, so that it resembles a hammer. A claw toe is a toe that is contracted at the PIP and DIP joints due to tightening of ligaments and tendons causing the joints to curl downwards. Claw toes may occur in any toe, except the big toe. A mallet toe is a deformity where the most distant joint points downward; mostly common in a patient's second toe whose second toe is the longest toe. A painful callous can form at the tip of a mallet toe.

Treatment for the above deformities depends on the severity of the deformity. Conservative treatment starts with new shoes that have soft, roomy toe boxes; the treatment may involve toe exercises to stretch and strengthen the muscles. In some cases, surgery—arthroplasty, arthrodesis—may be necessary if the toe deformity causes chronic pain. Surgical treatments are aimed at loosening up the contracted toe joints to allow them to align properly or at fusing the bones to prevent a recurrence of the problem.

Arthroplasty is a surgical procedure used to treat toe deformities in which a podiatric surgeon makes an incision along the toe and trims the head of the proximal phalanx, allowing the toe to straighten. Arthrodesis is a surgical procedure used to fuse two bones together, typically the proximal and middle phalanges. A podiatric surgeon removes the cartilage from the base of the middle phalanx and fixes the bones together with a removable pin.

A commonly used device in surgical procedures is a metal K-wire, which protrudes through the tip of the toe and may be removed as an outpatient several weeks after the surgery. The disadvantages of this technique is the inconvenience, the potential infection associated with the protruding wire and late flexion deformity at the proximal interphalangeal joint as a result of delayed union at the joint.

Thus, there is a need for an apparatus and a surgical technique that is simple, flexible and is performed by a minimally invasive lateral approach, for arthroplasty and/or the fusion of the proximal, middle and distal phalanx of the toe.

SUMMARY OF THE INVENTION

The present invention overcomes the disadvantages of the prior art and fulfills the needs noted above by providing an apparatus and surgical procedures for arthroplasty and/or fusion of the phalanx of the toe using a bioabsorbable pin. Bioabsorbable pins have several advantageous features: radiolucency; elastic modulus closer to that of the bone; and elimination of the need for removal subsequent to an implant.

Generally, the surgical procedure may be performed under local anesthesia, i.e., an injection of Liodocaine, Marcaine or Dexamethoasone.

The present invention includes an apparatus for use in the repair of toe deformities. The apparatus is a kit of parts and includes a pin, a predrill, a bone tamp, a cutter and a forceps. For example, a kit of parts known in the art includes a predrill, a bone tamp, and a 2.0 mm×100 mm bioabsorbable pin. The cutter may preferably be a Hot Loop Cutter, and the forceps may preferably be Bone Cutting Forceps, sold by Arthrex, Inc. of Naples, Fla.

The pin has a distal portion and a proximal portion. The proximal portion preferably is formed of a bioabsorbable material and the distal portion preferably is a metal. A distal end of the pin's distal portion is attached to a trocar tip and the distal portion may be removed once the pin is in place in the body (human or animal). The distal portion is graduated with laser marking to aid in measuring the drilling depth. The proximal portion has a V-shaped notch, which allows the pin's proximal portion to separate from the distal portion.

The present invention also includes surgical methods for repairing deformities in toes using a bioabsorbable pin. In one surgical method of PIP joint arthrodesis, the PIP joint is resected with an oscillating saw or rongeur. A proximal portion of the pin is seated in a pin driver. A hole in a proximal phalanx/phalange is drilled using the pin driver and the depth of the hole is measured using the distal portion of the pin. The pin is then removed from the proximal phalanx. A hole is drilled in a middle phalanx/phalange until the pin meets with resistance at a DIP cortex. The depth of the drilled hole in the middle phalanx is measured using the distal portion of the pin. The pin is removed from the middle phalanx. The length of the proximal portion of the pin is set to be the sum of the values of the proximal phalanx depth and the middle phalanx depth, and the distal portion is cut off. The pin is placed in the proximal and middle phalanxes to join the phalanxes. The exit wound is sutured at the PIP joint.

In another surgical method of PIP joint arthrodesis, a hole is drilled in the proximal phalanx using the pin driver, as explained above. The tip of the toe is drilled through the middle and distal phalanxes/phalanges. Without removing the pin from the toe, the pin length from the notch away from the trocar tip is measured using a ruler and the excess portion of the pin is cut off with a cutter. The pin in the pin driver is reversed, and the trocar tip is seated inside the pin driver. The pin is driven distal to proximal, traversing the distal, middle and proximal phalanxes/phalanges, until the pin stops advancing due to resistance at the junction of the proximal cortex. The pin is retracted distally by about 5 mm. The pin is clamped using forceps at the junction of the proximal and middle phalanxes/phalanges. The pin is cut flush with a cutter and a tamp is used to countersink the pin below the surface of the skin. The exit wound is sutured at the tip of the toe and at the PIP joint.

In yet another surgical method of PIP joint arthrodesis, a hole is drilled in the proximal phalanx using the pin driver, as explained above. A hole is drilled in the middle phalanx but not through the DIP joint. The depth of the hole is measured and length of the middle phalanx is set to the value of the measured depth. Subsequent to recording the middle phalangeal depth, the pin is drilled through the distal phalanx/phalange, leaving the V-shaped notch on the proximal portion exposed between the PIP joint. Without removing the pin from the toe, the pin length away from the notch is measured using a ruler and is set to the sum of the lengths of the proximal and middle phalanxes/phalanges. The excess portion of the pin's proximal portion is cut off with a cutter leaving a tapered end for easy insertion in the proximal phalanx/phalange. The pin in the pin driver is reversed, and the trocar tip is seated inside the pin driver. The pin is driven distal to proximal, traversing the distal, middle and proximal phalanxes/phalanges, until the pin stops advancing due to resistance at the junction of the proximal cortex. The V-shaped notch must be just proximal to the DIP joint. The pin is firmly held at the PIP joint using a forceps. The pin driver, with the distal portion engaged in the driver, is powered but not substantially advanced to automatically separate the pin at the V-shaped notch. The pin driver with the pin's separated portion is retracted from the distal phalanx/phalange. The toe is bent to normal anatomic position and the exit wound is sutured at the PIP joint.

In a surgical method of repairing an MTP joint, an incision is made over a first metatarsal phalangeal (MTP) joint and the soft tissues are released. The bump of the bone, i.e., the bunion, is removed from the side of the first metatarsal head. Using a predrill, a pilot hole is created in the first metatarsal by drilling below a dorsal medial surface of the first metatarsal head and directing it at a lateral and plantar declination of about 25 degrees. A proximal portion of a first pin is seated in a pin driver. The first pin is driven through the pilot hole by directing the pin toward a long axis of the first metatarsal shaft and inferior and distal portion of the first metatarsal. The distal portion is cut off and the pin is drilled retrograde until it rests flush with the plantar cortex of the metatarsal head. The proximal portion of the first pin is cut flush with a cutter. A second pin is placed perpendicular to the first pin by drilling the second pin in a plantar to dorsal direction from a lateral and distal portion of the first metatarsal. The exit wound is sutured at the MTP joint.

In yet another surgical method, an incision, for example, a V-cut, is made over a first metatarsal phalangeal (MTP) joint in a lateral plane, the distal end of the incision preferably being about 5 mm from the articular surface, with the dorsal arm being longer than the plantar arm. The angle of the V-cut is preferably about 35 degrees to about 60 degrees. The bump of the bone, i.e., the bunion, is removed from the side of the first metatarsal head. A pilot hole is created in the first metatarsal in a medial to lateral direction using a predrill. A proximal portion of a pin is seated in a pin driver. The pin is driven through the pilot hole until a distal portion of the pin exits past the plantar cortex. The distal portion of the pin is cut off using a cutter. The pin is drilled retrograde until the pin rests flush with the plantar cortex of the first metatarsal head. The proximal portion of the pin is cut flush with a cutter. The exit wound is sutured at the MTP joint.

BRIEF DESCRIPTION OF THE DRAWINGS

FIGS. 2A-H illustrate a surgical method for repairing deformities in toes, according to the present invention;

DETAILED DESCRIPTION OF THE PREFERRED EMBODIMENTS

The present invention relates to an apparatus and surgical methods for repair of toe deformities using a bioabsorbable pin by arthroplasty or fusion of proximal, middle and distal phalanx of the toe.

The term "bioabsorbable," as used herein, refers to materials which are absorbed by the body (human or animal) after chemical degradation, thus removing the need to surgically remove them from the body. Such materials include poly (p-dioxanone), polylactide (PLA), poly L-Lactide (PLLA), polyglycolic acid (PGA), polyglycolides, polycaprolactone, polyhydroxybutyrate (PHB), poly (orthoesters) and trimethylene carbonate polymer and the like, as well as copolymers, mixtures and/or blends of the same. The bioabsorbable materials may exhibit favorable degradation characteristics which ensure a high time zero strength that is maintained during the critical 12-week healing stage.

Figure 1A:
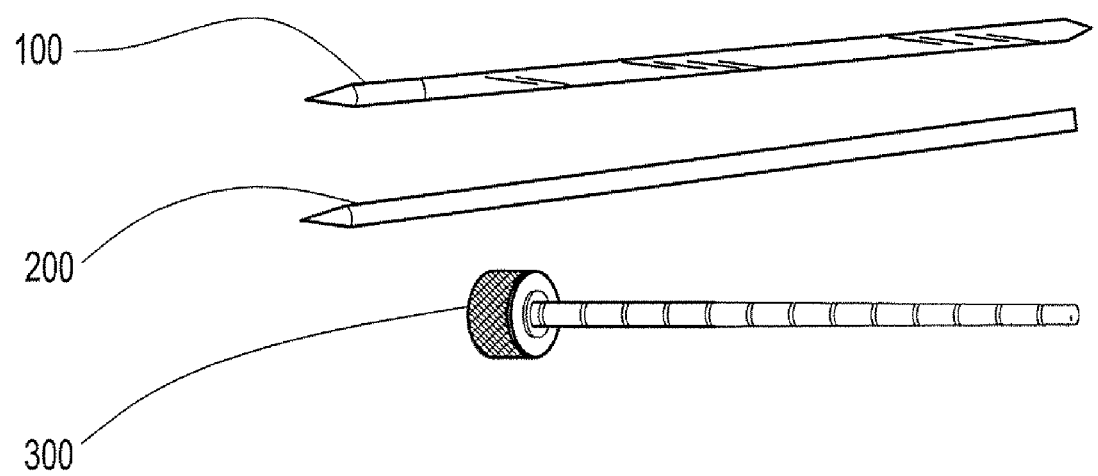
FIGS. 1A-B illustrate an apparatus as a kit of parts, according to the present invention.

Referring to FIG. 1A, the present invention is carried out using a pin 100 having dimensions of 2.0 mm×100 mm, for example, a predrill 200, a bone tamp 300, a cutter (not shown) and a forceps (not shown). The cutter may preferably be a Hot Loop Cutter, and the forceps may preferably be a Bone Cutting Forceps, sold by Arthrex, Inc. of Naples, Fla.

Figure 1B:
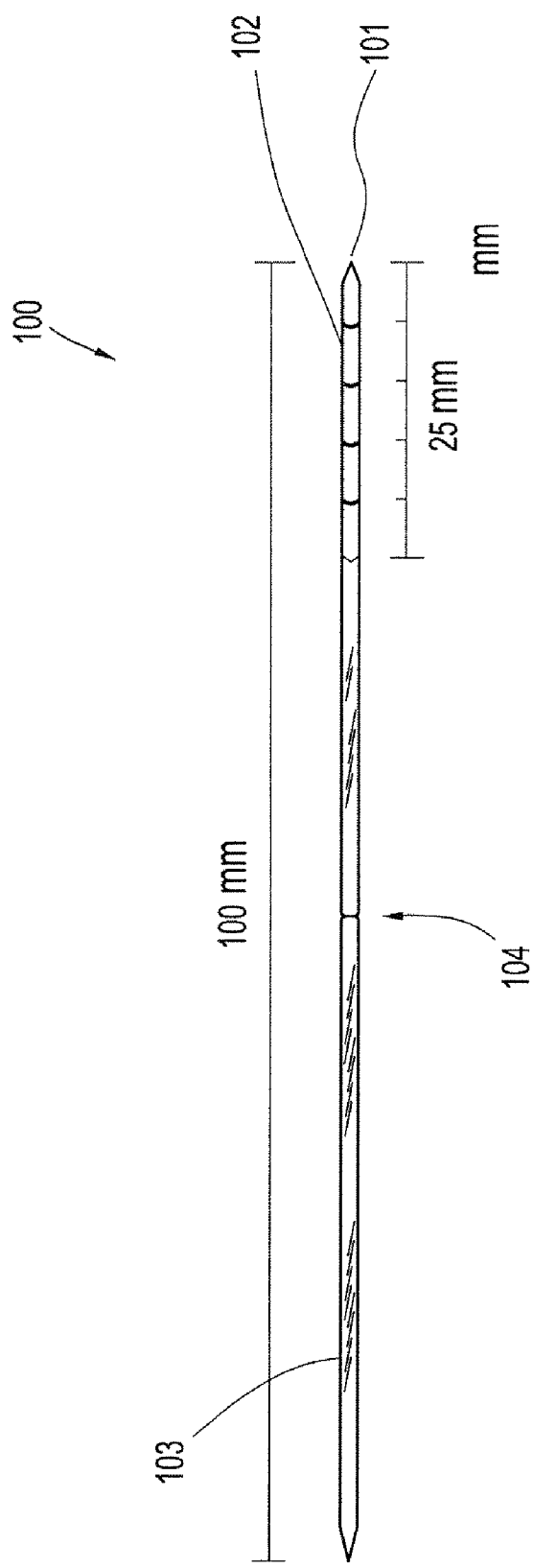

Referring to FIG. 1B, the pin 100 has a proximal portion 103 and a distal portion 102. The proximal portion 103 of the pin 100 is made of a bioabsorbable material. The distal portion 102 of the pin 100 is made of a material capable of penetrating bone, for example, metal and the distal portion 102 may be removed once the pin 100 is in place in a body (human/animal). The distal portion 102 of the pin 100 is preferably about 25 mm long and is graduated with laser markings, preferably every 5 mm, to aid in measuring the drilling depth. The proximal portion 103 has a V-shaped notch 104, which allows the proximal portion 103 of the pin 100 to separate from the distal portion 102. The distal and proximal portions 102, 103 preferably have uniform cross sections along their lengths and are connected to each other by screws or any other securing means known in the art.

A trocar tip 101, i.e., a three-sided tip with a long bevel, is attached to a distal end of the distal portion 102 of the pin 100. The trocar tip 101 is preferably made of a material such as stainless steel, titanium, cobalt-chromium-molybdenum, implant grade metal alloys, zirconia, aluminum oxide, carbon/carbon composites or the like. The trocar tip 101 is preferably fixed to the distal end of the distal portion 102 of the pin 100 by screws or any other securing means known in the art.

By using a standard quick connect pin driver 105 (FIG. 2A), the surgeon can drill and place the pin 100 in one step. The proximal portion 103 of the pin 100 is seated in the pin driver 105 (FIG. 2A) during the drilling phase. The distal portion 102 is drilled past the far cortex and cut off with the bone cutting forceps or hot loop cutter.

In cases with hard bone stock, a metal "predrill" pin K-Wire is used to create a pilot hole. The graduated bone tamp is used to countersink the pin below the skin and bone surface.

Surgical Techniques

1. Bunionectomy

Figure 2A:
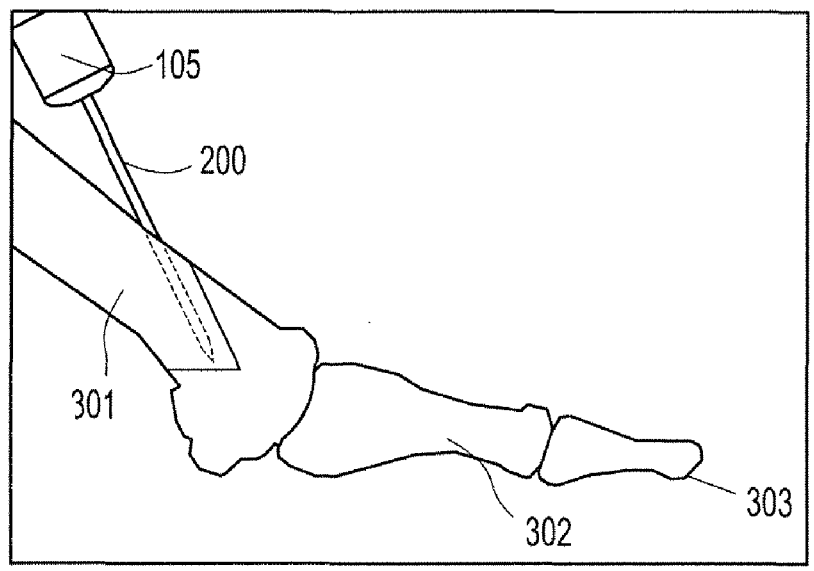

FIGS. 2A-2H show the surgical procedure for one type of bunionectomy. An incision is made over a first metatarsal phalangeal (MTP) joint and the soft tissues are released. The bump of the bone, i.e., the bunion, is removed from the side of the first metatarsal head. Referring to FIG. 2A, using a predrill 200, a pilot hole is created by drilling to a laser line in the first metatarsal by drilling below a dorsal medial surface of the first metatarsal head and directing it at a lateral and plantar declination of about 25 degrees.

Figure 2B:
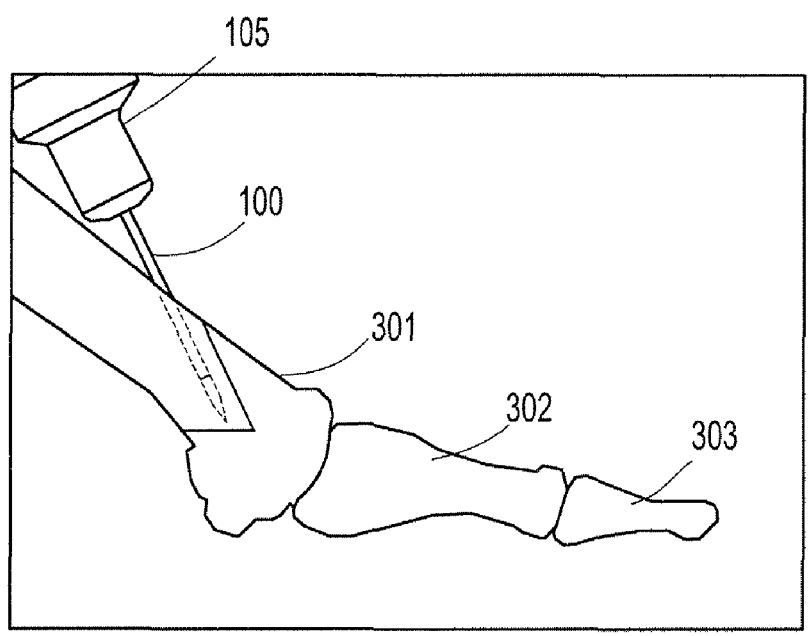

A proximal portion of a first pin 100 is seated in the pin driver 105. The first pin 100 is seated in the pin driver 105 about 1 cm past the trocar tip of the first pin 100, as shown in FIG. 2B. The pin driver 105 should accept a pin, preferably a 2 mm pin. A "Jacobs Chuck" connection should not be used.

Referring to FIGS. 2C-2D, the first pin 100 is advanced gradually, carefully reseating the first pin 100 in the pin driver 105 as the first pin 100 advances through the bone. The weight of the pin driver 105 is used to slowly advance the first pin 100 toward a long axis of the first metatarsal shaft and inferior and distal portion of the first metatarsal. The first pin 100 is advanced through the plantar soft tissues and the proximal portion of the first pin is cut with a cutter, as shown in FIG. 2E. Alternatively, the trocar tip 101 is advanced past the plantar cortex and the distal portion of the pin is cut using either a bone-cutting forceps or a cutter 500, as shown in FIG. 2F.

Figure 2G:
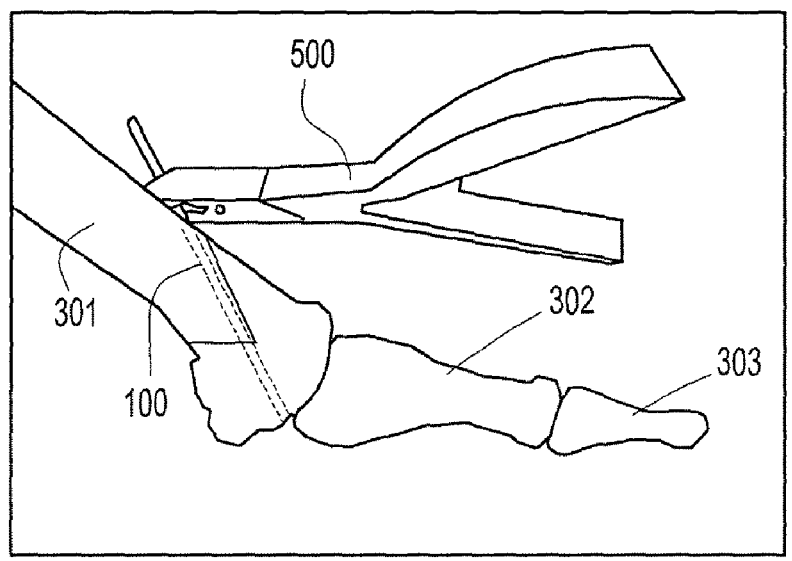
Figure 2H:
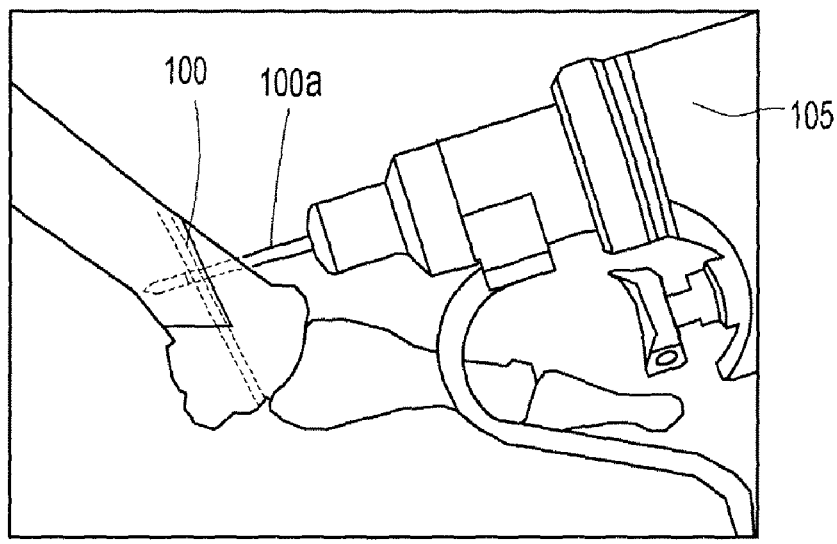

Referring to FIG. 2G, the first pin 100 is drilled retrograde until it rests flush with the plantar cortex of the metatarsal head. The proximal portion of the first pin 100 is cut flush with a bone-cutting forceps or a cutter 500. To improve the stability of the construct, a second pin 100a is placed perpendicular to the first pin 100, as shown in FIG. 2H, by drilling the second pin 100a in a plantar to dorsal direction from a lateral and distal portion of the first metatarsal. The exit wound is sutured at the MTP joint.

In yet another surgical procedure for bunionectomy, an incision, for example, a V-cut, is made over a first metatarsal phalangeal (MTP) joint in a lateral plane, the distal end of the incision preferably being about 5 mm from the articular surface, with the dorsal arm being longer than the plantar arm. The angle of the V-cut is preferably about 35 degrees to about 60 degrees. The bump of the bone, i.e., the bunion, is removed from the side of the first metatarsal head. A pilot hole is created in the first metatarsal in a medial to lateral direction using a predrill. A proximal portion of a pin is seated in a pin driver. The pin is driven through the pilot hole until a distal portion of the pin exits just past the plantar cortex. The distal portion of the pin is cut flush to the bone using a cutter. The pin is drilled retrograde until the pin rests flush with the plantar cortex of the first metatarsal head. The proximal portion of the pin is cut flush with a cutter. The exit wound is sutured at the MTP joint.

2. Proximal Interphalangeal Joint Resection

Figure 3A:
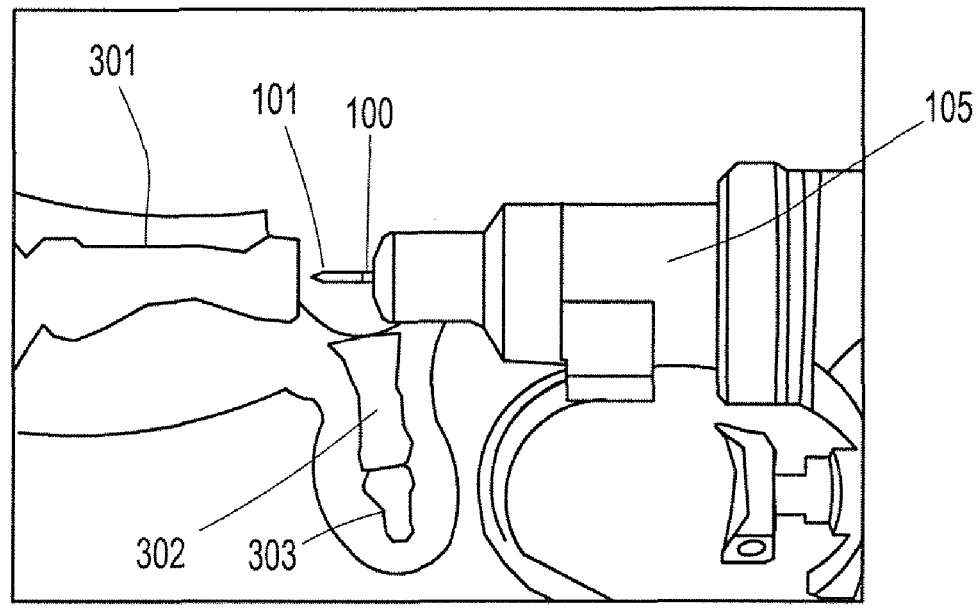
FIGS. 3A-F illustrate a surgical method of PIP joint repair, according to the present invention.

FIGS. 3A-3F show a surgical procedure for proximal interphalangeal joint resection. Referring to FIG. 3A, after resecting the joint with an oscillating saw or rongeur, a proximal portion 103 (FIG. 1B) of a pin 100 is seated in a pin driver 105, no further than 1 cm past the back of the trocar tip 101.

Figure 3B:
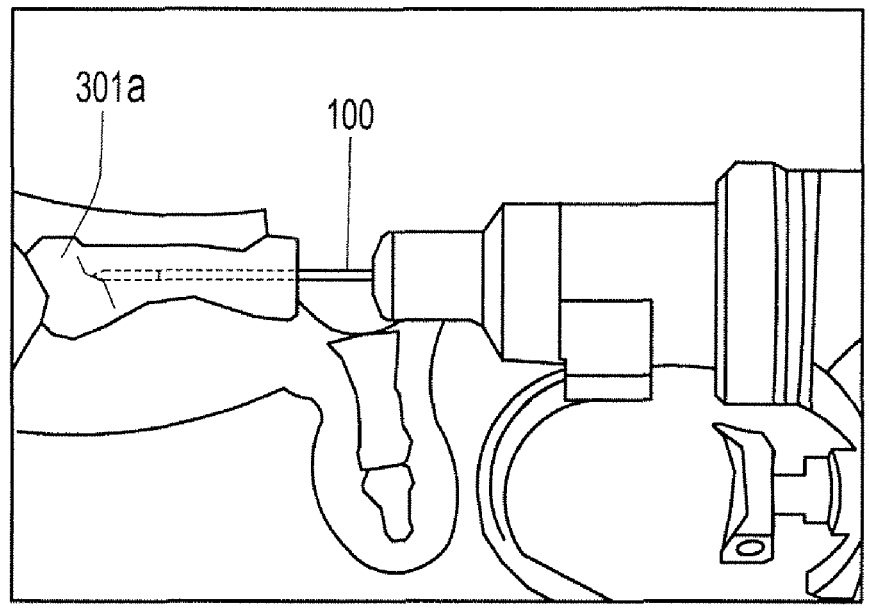

The pin 100 is gradually advanced through the proximal phalanx 301. The pin driver 105 is advanced slowly, reseating the pin 100 every 10-15 mm. The depth of the hole created by the pin 100 is measured using a distal portion 102 (FIG. 1B) of the pin 100. The pin 100 is advanced in the proximal phalanx 301 stopping just prior to a proximal cortical wall 301a, as shown in FIG. 3B. The pin 100 is removed from the proximal phalanx 301.

Figure 3C:
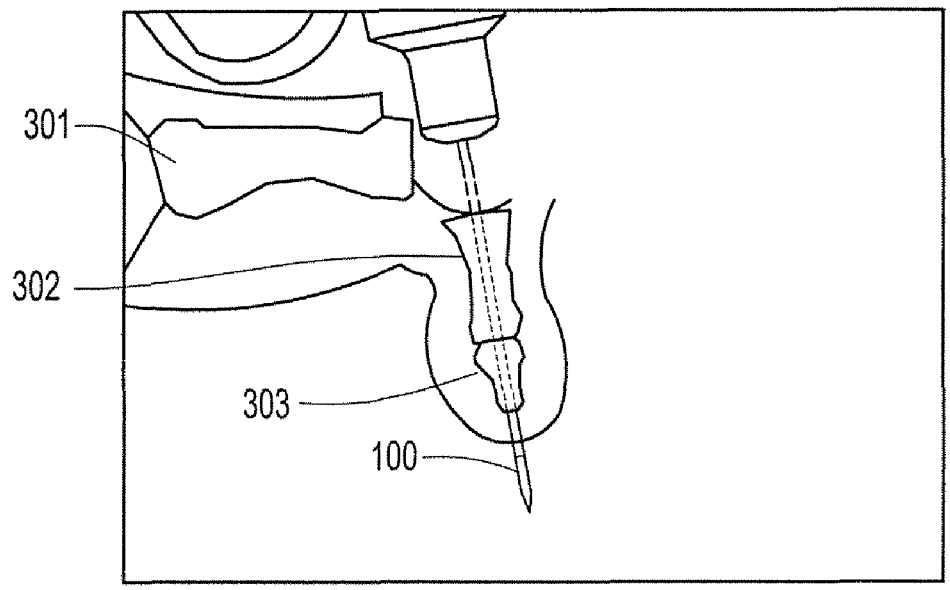

A hole is drilled in a middle phalanx/phalange 302 (FIG. 3C) until the pin 100 meets with resistance at a DIP cortex. The depth of the drilled hole is measured in the middle phalanx 302 (FIG. 3C) using the distal portion 102 (FIG. 1B) of the pin 100. The pin 100 is removed from the middle phalanx 302 (FIG. 3C). The length of the proximal portion 103 (FIG. 1B) of the pin 100 is set to be the sum of the values of the proximal phalanx depth and the middle phalanx depth and the distal portion 102 (FIG. 1B) is cut off. The pin 100 is placed in the proximal and middle phalanxes 301, 302 (FIGS. 3A, 3C) to join the phalanxes. The exit wound is sutured at the PIP joint.

In yet another surgical procedure for proximal interphalangeal joint, a hole is drilled in the proximal phalanx 301 using the pin driver 105, as explained above. Referring to FIG. 3C, with the pin 100 still seated in the pin driver 105, the tip of the toe is drilled through the middle and distal phalanxes/phalanges 302, 303. The distal portion of the pin 100 should be exposed by at least 15 mm. Without removing the pin 100 from the toe, the pin length from the notch away from the trocar tip is measured using a ruler and the excess portion of the pin is cut off with a cutter.

Figure 3D:
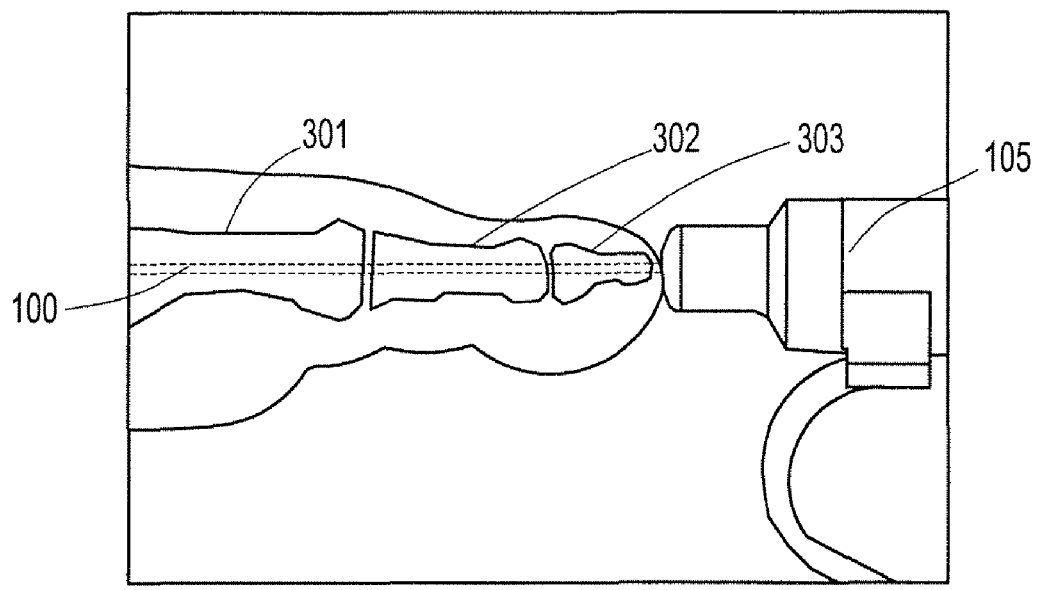
Figure 3E:
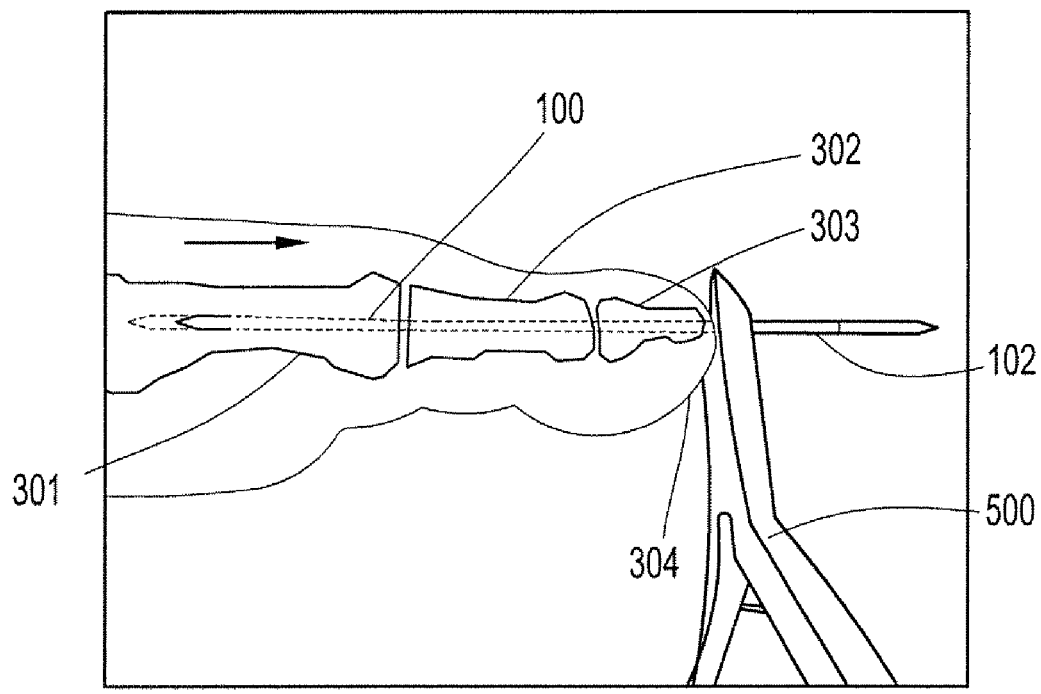

The pin 100 is reversed in the pin driver 105 and the trocar tip 101 (FIG. 1B) is seated inside the pin driver 105. The pin 100 is gradually drilled retrograde with the proximal portion of the pin 100 traversing the distal, middle and proximal phalanges 301, 302, 303, as shown in FIG. 3D. Once the pin 100 meets resistance at the junction of the proximal cortex, the pin 100 is retracted distally 5 mm, as shown in FIG. 3E. The pin 100 is clamped using forceps at the junction of the proximal and middle phalanxes/phalanges 301, 302. The pin 100 is cut flush with a hot-loop cutter 304 or bone-cutting forceps (not shown).

Figure 3F:
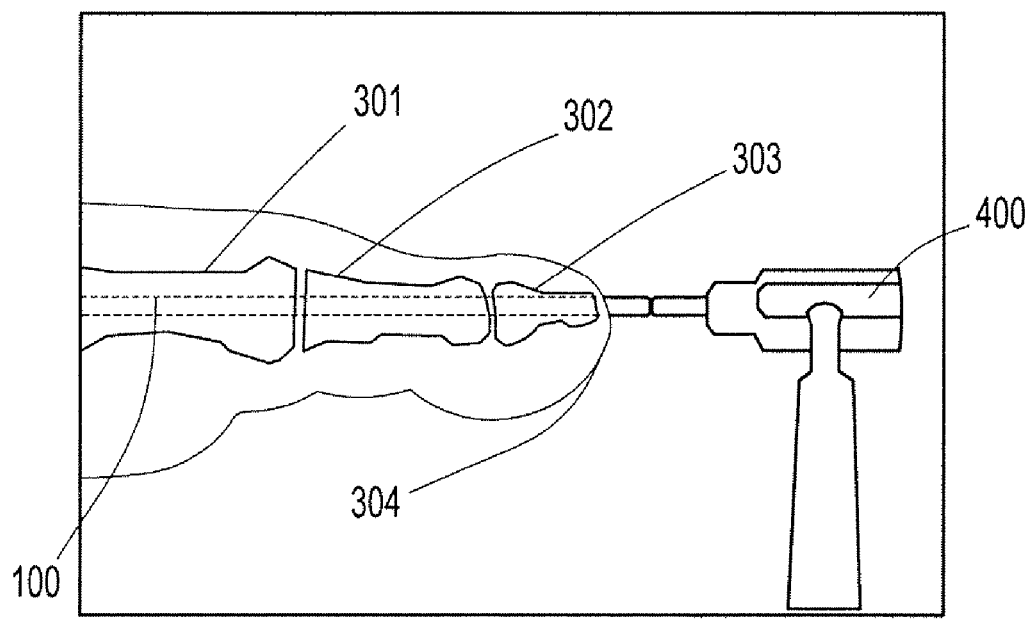

Finally, a tamp 400 is used to countersink the pin 100 below the surface 304 of the skin, as shown in FIG. 3F. The exit wound is sutured at the tip of the toe and at the PIP joint.

FIGS. 4A-4F show yet another surgical procedure for proximal interphalangeal joint resection. After resecting the joint with an oscillating saw or rongeur, a proximal portion 103 (FIG. 1B) of a pin 100 is seated in a pin driver 105, no further than 1 cm past the back of the trocar tip 101.

Figure 4A:
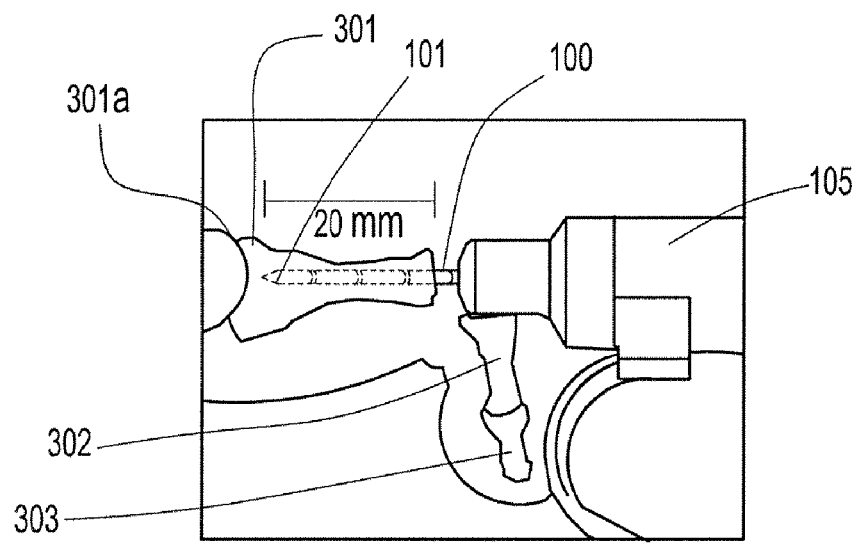
FIGS. 4A-4F illustrate a surgical method of PIP joint repair, according to the present invention.

Referring to FIG. 4A, the pin 100 is gradually advanced through the proximal phalanx 301. The pin driver 105 is advanced slowly, reseating the pin 100 every 10-15 mm. The depth of the hole created by the pin 100 is measured using laser markings provided on a distal portion 102 (FIG. 1B) of the pin 100. The pin 100 is advanced in the proximal phalanx 301 stopping just prior to a proximal cortical wall 301a The pin 100 is removed from the proximal phalanx 301.

Figure 4B:
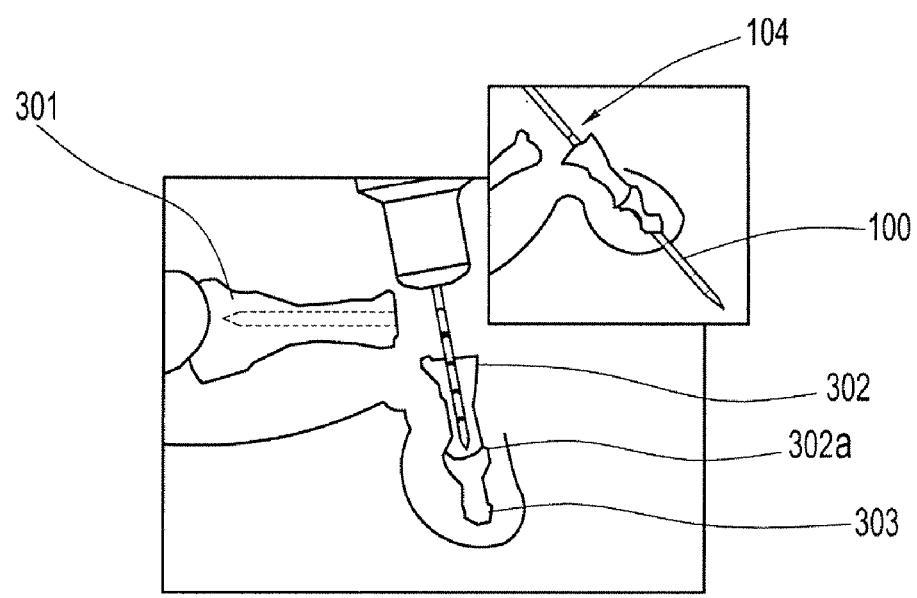
Figure 4C:
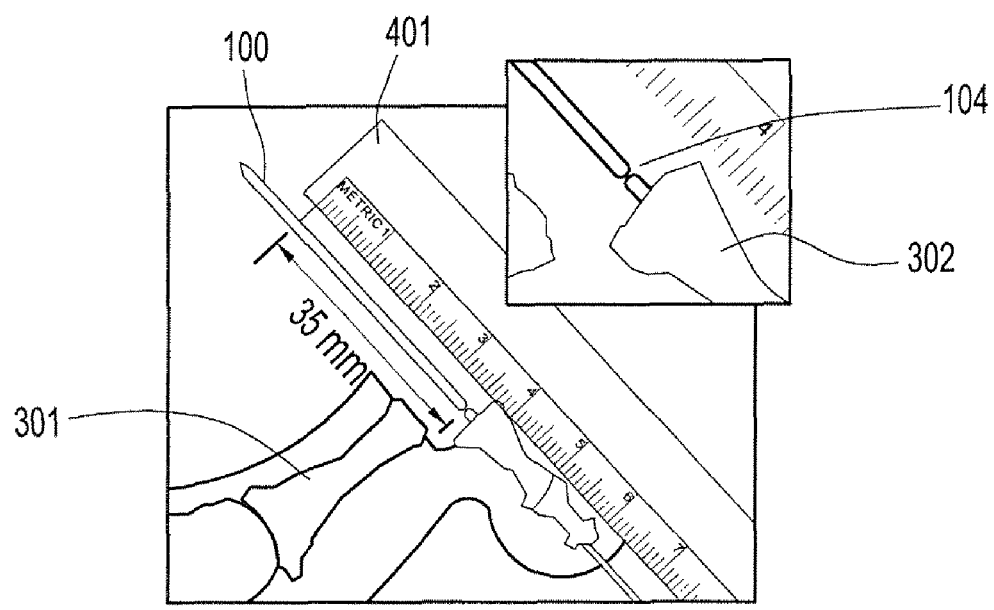

Referring to FIG. 4B, a hole is drilled in a middle phalanx/phalange 302 but not through the DIP joint 302a. The depth of the drilled hole is measured in the middle phalanx 302 using the distal portion 102 (FIG. 1B) of the pin 100. The length of the middle phalanx is set to the value of the measured depth. Subsequent to recording the middle phalangeal depth, the pin 100 is drilled through the distal phalanx/phalange 303, leaving the V-shaped notch 104 on the proximal portion exposed between the PIP joint, as shown in FIG. 4C. Without removing the pin 100 from the toe, the pin length away from the V-shaped notch 104 is measured using a ruler 401 and is set to the sum of the lengths of the proximal and middle phalanxes/phalanges 301, 302.

Figure 4D:
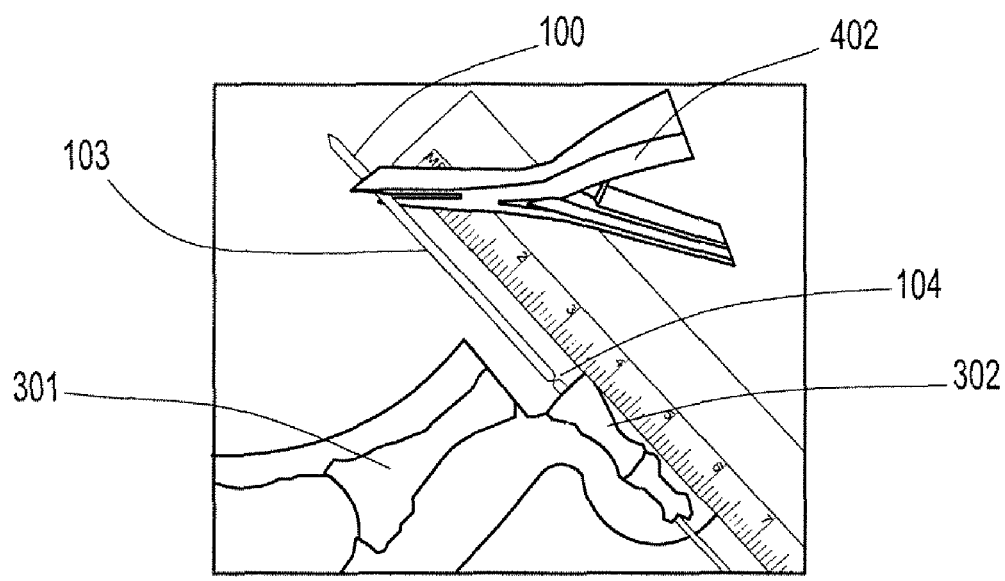

Referring to FIG. 4D, the excess portion of the pin's proximal portion 103 is cut off with a cutter 402 leaving a tapered end for easy insertion in the proximal phalanx/phalange 301. The tapered end of the proximal portion 103 is placed in the proximal phalange 301.

Figure 4E:
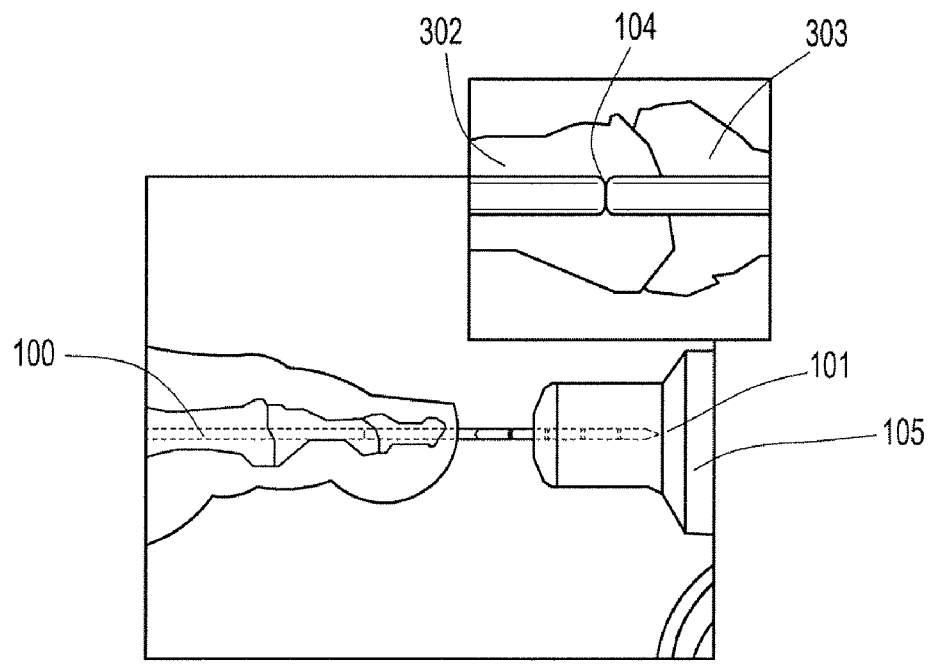
Figure 4F:
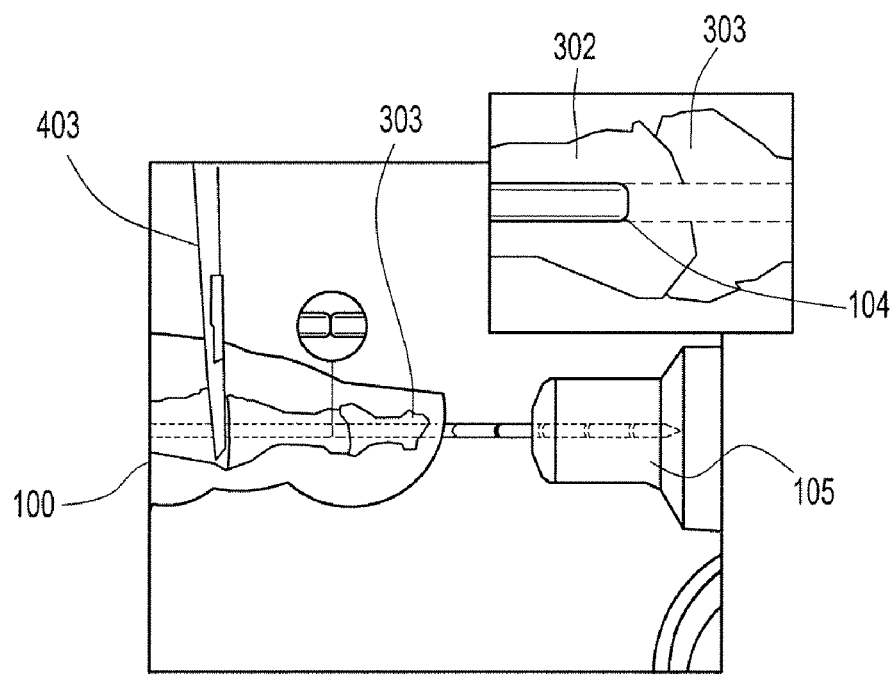

Referring to FIG. 4E, the pin 100 in the pin driver is reversed, and the trocar tip 101 is seated inside the pin driver 105. The pin is driven distal to proximal, traversing the distal, middle and proximal phalanxes/phalanges 301, 302, 303, until the pin stops advancing due to resistance at the junction of the proximal cortex. The V-shaped notch 104 must be just proximal to the DIP joint. The pin 100 is firmly held at the PIP joint using a forceps 403, as shown in FIG. 4F. The pin driver 105, with the distal portion engaged in the driver, is powered but not substantially advanced to automatically separate the pin 100 at the V-shaped notch 104. The pin driver 105 with the pin's separated portion is retracted from the distal phalanx/phalange 303. The toe is bent to its normal anatomic position and the exit wound is sutured at the PIP joint.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A method of repairing bunions using a first pin comprising:
    making an incision over a first metatarsal phalangeal joint;
    removing bunions from a side of a first metatarsal head;
    drilling a pilot hole in a first metatarsal below a dorsal medial surface of the first metatarsal head at a lateral and plantar declination;
    advancing a distal portion of the first pin in the pilot hole toward a long axis of a first metatarsal shaft at an inferior and distal portion of the first metatarsal such that a trocar tip of the first pin advances past a plantar cortex, the first pin having a proximal portion made of a bioabsorbable material;
    cutting the distal portion of the first pin and drilling retrograde until the first pin rests flush with the plantar cortex of the first metatarsal head; and
    cutting the proximal portion of the first pin flush to the first metatarsal.

2. The method of claim 1, further comprising:
    drilling a second pin in a plantar to dorsal direction from a lateral and distal portion of the first metatarsal, the second pin being perpendicularly positioned to the first pin; and
    suturing the incision over the first metatarsal phalangeal joint.

3. The method of claim 1, wherein the bioabsorbable material comprises poly (p-dioxanone), polylactide (PLA), poly L-Lactide (PLLA), polyglycolic acid (PGA), polyglycolides, polycaprolactone, and polyhydroxybutyrate (PHB).

4. A method of repairing bunions using a pin comprising:
    making a V-cut incision over a first metatarsal phalangeal joint in a lateral plane;
    removing bunions from a side of a first metatarsal head;
    drilling a pilot hole in a first metatarsal in a medial to lateral direction;
    advancing the pin through the pilot hole until a distal portion of the pin exits past a planar plantar cortex;
    cutting the distal portion of the pin and drilling retrograde until the pin rests flush with the plantar cortex of the first metatarsal head, the pin having a proximal portion made of a bioabsorbable material comprising poly L-Lactide (PLLA);
    cutting the proximal portion of the pin flush to the first metatarsal; and
    suturing the V-cut incision at the metatarsal phalangeal joint.

5. A method of repairing a proximal interphalangeal joint using a pin comprising:
    resecting the joint using a cutting instrument, the cutting instrument being one of a saw or rongeur;
    drilling a hole in a proximal phalanx to a first depth using a pin driver by advancing a distal portion of the pin through the proximal phalanx up to a proximal cortical wall, and subsequently removing the pin from the proximal phalanx;
    drilling a hole in a middle phalanx to a second depth until the pin meets with resistance at a DIP cortex, and setting a length of a proximal portion of the pin, the proximal portion being made of a bioabsorbable material; and
    placing the pin in the proximal and middle phalanxes, and suturing wound at the joint.

6. The method of claim 5, wherein the length of the proximal portion is set to be a sum of the first and second depths.

7. A method of repairing a proximal interphalangeal joint using a pin comprising:
    resecting the proximal interphalangeal joint;
    drilling a hole in a proximal phalanx using a pin driver by advancing a distal portion of the pin through the proximal phalanx up to a proximal cortical wall, and subsequently removing the pin from the proximal phalanx;
    drilling the pin through middle phalange but not through distal interphalangeal joint to create a second hole and measuring the second hole's depth;
    drilling the pin through distal phalange of the joint by distally advancing the distal portion such that a notch on the proximal portion of the pin is exposed between the proximal interphalangeal joint;
    setting the length from the notch to the proximal portion of the pin to sum of lengths of the proximal and middle phalanges, and cutting off excess portion of the pin's proximal portion;
    seating the proximal portion of the pin in the hole in the proximal phalanx and subsequently drilling retrograde such that the proximal portion traverses the distal, middle and proximal phalanges to a proximal cortex such that the notch is proximal to the distal interphalangeal joint;
    separating the pin at the notch; and
    retracting separated portion of the pin from the distal phalange, and suturing exit wound,
    wherein the proximal portion of the pin is made of a bioabsorbable material.

8. The method of claim 7, wherein the bioabsorbable material comprises Poly L-Lactide.

9. The method of claim 7, wherein the notch is V-shaped.

* * * * *